United States Patent [19]

Hertel et al.

[11] Patent Number: 5,430,026
[45] Date of Patent: Jul. 4, 1995

[54] 2'-DEOXY-2',2'-DIFLUORO (4-SUBSTITUTED PYRIMIDINE) NUCLEOSIDES, BICYCLIC DERIVATIVES, PHARMACEUTICAL COMPOSITIONS, AND SYNTHETIC PRECURSORS

[75] Inventors: Larry Hertel; Julian S. Kroin, both of Indianapolis, Ind.

[73] Assignee: Eli Lilly and Company, Indianapolis, Ind.

[21] Appl. No.: 146,368

[22] Filed: Oct. 29, 1993

Related U.S. Application Data

[62] Division of Ser. No. 902,314, Jun. 22, 1992, abandoned.

[51] Int. Cl.$^6$ .................... A61K 31/70; C07H 19/067; C07H 19/23
[52] U.S. Cl. ........................................ 514/43; 514/45; 514/49; 514/50; 536/27.13; 536/28.4; 536/28.5; 536/28.53
[58] Field of Search ................. 536/27.13, 28.5, 28.53; 514/43, 45, 49, 50

[56] References Cited

U.S. PATENT DOCUMENTS

| | | | |
|---|---|---|---|
| 4,526,988 | 7/1985 | Hertel | 549/313 |
| 4,692,434 | 9/1987 | Hertel | 514/49 |
| 4,965,374 | 10/1990 | Chou et al. | 549/313 |
| 5,061,793 | 10/1991 | Grindey et al. | 536/45 |

FOREIGN PATENT DOCUMENTS

| | | | |
|---|---|---|---|
| 122707 | 3/1984 | European Pat. Off. | C07H 19/4 |
| 184365 | 11/1985 | European Pat. Off. | C07H 19/06 |
| 211354 | 7/1986 | European Pat. Off. | |
| 339161 | 4/1988 | European Pat. Off. | |
| 329348 | 2/1989 | European Pat. Off. | C07H 19/4 |
| 345751 | 6/1989 | European Pat. Off. | |
| 0328345 | 8/1989 | European Pat. Off. | 514/45 |
| 9115498 | 10/1991 | WIPO | 514/45 |

OTHER PUBLICATIONS

Miller et al., "Alkaloids of *Vinca rosea* L. (*Cantharanthus roseus* G. Don). 38. 4'-Dehydrated Derivatives," *J. Med. Chem.*, 20(3), 409–413 (1977).

Sweeney et al., "Antitumor Activity of Deacetyl Vinblastine Amide Sulfate (Vindesine) in Rodents and Mitotic Accumulation Studies in Culture," *Cancer Research*, 38, 2886–2891 (1978).

Watanabe, K. A., et al., Synthesis and Anti-HIV-1 Activity of 2'-"up"-Fluoro Analogues of Active Anti--AIDS Nucleosides 3'Azido-deoxythymidine (AZT) and 2',3'-Dideoxycytidine (DDC), *J. Med. Chem.* 33, 2145–2150 (1990).

Sterzycki, R. Z., et al., Synthesis and Anti-HIV-1 Activity of Several 2'-Fluoro Containing Pyrimidine Nucleosides, *J. Med. Chem.* 33, 2150–2157 (1990).

R. S. Root-Bernstein, "AiIDS is more than HIV: Part II", *Genetic Engineering News*, Sep. 15, 1992, pp. 4–5.

R. S. Root-Bernstein, "AIDS is more than HIV: Part I", *Genetic Engineering News*, Sep. 1, 1992, pp. 4–6.

*Primary Examiner*—Douglas W. Robinson
*Assistant Examiner*—L. Eric Crane
*Attorney, Agent, or Firm*—Robert A. Conrad

[57] ABSTRACT

The invention provides certain 2-Deoxy-2,2-Difluoro (4-Substituted) Pyrimidine Nucleosides that are effective as anti-cancer agents and in treating viral infections.

13 Claims, No Drawings

2'-DEOXY-2',2'-DIFLUORO (4-SUBSTITUTED PYRIMIDINE) NUCLEOSIDES, BICYCLIC DERIVATIVES, PHARMACEUTICAL COMPOSITIONS, AND SYNTHETIC PRECURSORS

This application is a division, of application Ser. No. 07/902,314, filed Jun. 22, 1992, now abandoned.

BACKGROUND OF THE INVENTION

1. Field of the Invention

The invention relates to substituted pyrimidine nucleosides having anti-tumor and anti-viral activity and a method for using same.

2. State of the Art

While the treatment of cancer was once considered impossible, great strides have been made during the past ten years in controlling the ravages of this often fatal disease. Several drugs which contribute to the increasing rate of survival are now routinely used clinically. Commonly employed anti-tumor agents include methotrexate, doxorubicin, vinca alkaloids such as vincristine, and pyrimidine nucleosides. Deoxy-difluoro pyrimidine nucleosides exhibiting anti-tumor activity have been described in European Patent Application Nos. 329,348; 339,161; 184,365; and 211,354.

Anti-viral agents are also found among the general family of nucleosides. For example, 1-(2-deoxy-2-fluoro-β-D-arabinofuranosyl)thymine (FMAU) and 1-(2-deoxy-2-fluoro-β-D-arabinofuranosyl)-5-iodocytosine (FIAC) have been described by Watanabe, K.A., et. al., in the Synthesis and Anti-HIV-1 Activity of 2'-"Up"-Fluoro Analogues of Active Anti-AIDS Nucleosides 3'-Azido-3'-deoxythymidine (AZT) and 2',3'-Dideoxycytidine (DDC), J. Med. Chem., 33, p 2145–2150 (1990) as potent anti-herpetics. Also, 2'-deoxy-2'-fluoroarabino-5-iodouridine (FIAU) has been described by Sterzycki, R. Z.,et. al., in the Synthesis and Anti-HIV-1 Activity of Several 2'-Fluoro Containing Pyrimidine Nucleosides, J. Med. Chem., 33, p 2150–2157 (1990) as being effective against human immunodeficiency virus (HIV). Deoxy-difluoro pyrimidine nucleosides exhibiting anti-viral activity have been described in European Patent Applications 345,751; 122,707; and 339,161; and U.S. Pat. Nos. 4,526,988; 4,965,374; and 4,692,434.

However, research continues to develop more effective compounds with greater safety for subjects under treatment.

Accordingly, it is an object of the present invention to provide compounds for use in treating mammals suffering from disease states and disorders stemming from tumor and viral infections.

Another object of the present invention is to provide intermediate compounds for use in the preparation of novel compounds for treating mammals suffering from disease states and disorders stemming from tumor and viral infections.

Another object of the present invention is to provide therapeutic compositions for treating disease states and disorders stemming from tumor and viral infections.

Still another object of the present invention is to provide a method for treating disease states and disorders stemming from tumor and viral infections.

Other objects, features and advantages will become apparent to those skilled in the art from the following description and claims.

SUMMARY OF THE INVENTION

The invention is a compound of the formula

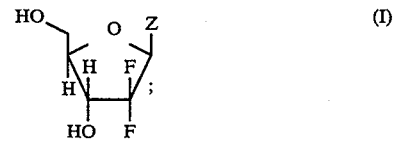

wherein z is a nucleobase selected from the group consisting of:

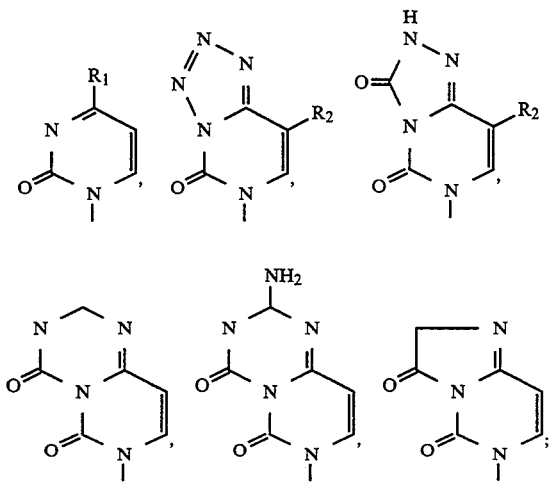

wherein $R_1$ is selected from the group consisting of glycine, thio, hydrogen, hydrazino, methylamino, 2-methylhydrazino, ethylhydrazino carboxylate, hydroxyamino, hydroxymethylamino, carboxylic acid, carboxylaldehyde, isocyano, cyanate, carboethoxyamino, aminosulfonyl, glycine ethyl ester, alanine ethyl ester, carbonitrile, nitro, carboxamido, aminothio, aminomethyl, and sulfonylamino; and $R_2$ is selected from the group consisting of hydrogen, methyl, bromo, fluoro, chloro, iodo, bromovinyl, and amino; and pharmaceutically acceptable salts thereof.

In another aspect, the invention is intermediates that are useful in the preparation of the compound of formula I.

In another aspect, the invention is pharmaceutical formulations containing the compound of formula I in association with a pharmaceutically acceptable carrier, diluent or excipient.

In another aspect, the invention is a method of treating susceptible neoplasms in mammals comprising administering to a mammal in need of such treatment a pharmaceutically effective amount of a compound of formula I.

In yet another aspect, the invention is a method of treating viral infections in mammals comprising administering to a mammal in need of such treatment an antivirally effective amount of a compound of formula I.

DETAILED DESCRIPTION OF THE INVENTION

The term "substituted" alone or in combination refers to substitution by at least one or more groups at the 4-position of the pyrimidine ring. The term "halo" alone or in combination refers to chloro, fluoro, bromo or iodo. The phrase "pharmaceutically effective amount" alone or in combination refers to an appropriate amount of a compound of formula I which is capable of providing chemotherapy to mammals. The phrase "anti-virally effective amount" alone or in combination refers to an appropriate amount of a compound of formula I which is capable of preventing or inhibiting the presence of viral infections in mammals. The phrase "susceptible neoplasm" alone or in combination refers to an abnormal growth of tissue in mammals capable of being treated by a compound of formula I. The phrase "inert solvent" alone or in combination refers to substances that provide a medium in which a reaction can occur but otherwise do not materially contribute to the reaction. The phrase "active ingredient" alone or in combination refers to a compound of formula I or a pharmaceutically acceptable salt thereof. The phrase "pharmaceutically acceptable" alone or in combination refers to a carrier, diluent or excipient compatible with the other ingredients of the formulation and not deleterious to the recipient thereof. The phrase "unit dosage form" alone or in combination refers to physically discrete units suitable as unitary dosages for human subjects and other mammals, each unit containing a predetermined quantity of active material calculated to produce the desired therapeutic effect, in association with a suitable pharmaceutical carrier.

The compound of formula I may be prepared by the procedure described in Synthesis of 2-Deoxy-2,2-difluoro-D-ribose and 2-Deoxy-2,2-difluoro-D-ribofuranosyl Nucleosides, Org. them., 53, 2406–2409 (1988). In general, the procedure requires preparing a β-1-(2-Oxo-4-(1,2,4-Triazol-1-yl)-1,2-dihydropyrimidin-1-yl -3,5-bis-O-(t-butYldimethylsilyl)-2-deoxy-2,2-difluororibose intermediate by treating D-1-(2,4-Dioxo-1,2,3,4-tetrahydropyrimidin-1-yl)-3,5-bis-O-(t-butyldimethylsilyl)-2-deoxy-2,2-difluororibose with 1,2,4-triazole and p-chlorophenyl dichlorophosphate in pyridine. The β-1-(2-Oxo-4-(1,2,4-Triazol-1-yl)-1,2-dihydropyrimidin-1-yl)-3,5-bis -O-(t-butyldimethylsilyl)-2-deoxy-2,2-difluororibose intermediate is then added to triethylamine along with a suitable nucleophile such as hydroxylamine hydrochloride in a solvent such as p-dioxane. The solvent is then removed and the residue dissolved in ethyl acetate and washed with water. The organic layer is dried in vacuo over sodium sulfate and concentrated in vacuo to yield a blocked intermediate compound of formula II.

If the nucleophile is a free base such as methylamine then the triethylamine may be eliminated. When ethyl carbamate is the nucleophile, 1 equivalent to 3 equivalents of sodium hydride or other suitable base and a solvent such as tetrahydrofuran are needed to activate the nucleophile when ethyl carbazate is the nucleophile, the reaction mixture is heated to about 70° C. for 3 hours to 15 hours in order to drive the reaction to completion. When the nucleophilic substitution includes an ester moiety such as glycine ethyl ester, the hydrolysis of the ester to a carboxylic acid is carried out using standard hydrolysis conditions such as sodium hydroxide, alcohol and water. when an azide moiety is employed as the nucleophile, the bicyclic compounds of formula I may be formed as described by C. Wentrup in Hetarylnitrenes II, Tetrahedron, 26, P 4969–4983 (1970). For example, a 4-azido substituent may cyclized on the pyrimidine ring to the 3 position. In the case of a 4-carbazate substituent, the cyclization is promoted by heating in the absence of solvent.

The hydroxy protecting group (X) suitable for use in the present invention may be chosen from known protecting groups used in synthetic organic chemistry. The hydroxy protecting group selected is preferably capable of being efficiently placed on the carbohydrate moiety and easily removed therefrom once the glycosylation reaction has been completed. Suitable hydroxy protecting groups known in the art are described in Chapter 3 of *ProteCtive Groups in Organic Chemistry*, McOmie Ed., Plenum Press, New York (1973), and Chapter 2 of *Protective Groups in Organic Synthesis*, Green, John, J. Wiley and Sons, New York (1981); preferred are acetyl and t-butyldimethylsilyl .

In attaching the hydroxy protecting groups to the carbohydrate moiety, typical reaction conditions are employed and depend on the nature of the protecting group chosen as discussed in U.S. Pat. No. 4,526,988 which is incorporated herein by reference.

The blocked intermediate is then deblocked by one of the following deblocking procedures, (A) thru (C):

In deblocking procedure (A), the blocked intermediate is dissolved under anhydrous conditions in dichloromethane and saturated with anhydrous hydrogen bromide at 0° C. to 5° C. The reaction mixture is then allowed to warm to room temperature. Next, the reaction mixture is concentrated in vacuo to an oil, dissolved in water and washed with ethyl acetate. The aqueous layer is evaporated in vacuo to yield a deblocked compound of formula I.

In deblocking procedure (B), the blocked intermediate is dissolved in tetrahydrofuran and treated at ambient temperature with tetrabutylammonium fluoride. After 1 hour, the solvent is removed, the product is dissolved in water and washed with ethyl acetate. The water is then removed in vacuo to yield a deblocked compound of formula I.

Finally, deblocking procedure (C) requires dissolving the blocked intermediate in methanol, cooling to ice bath temperatures and saturating with anhydrous ammonia. The reaction mixture is then stirred at room temperature for several hours after which the solvent is removed to yield a deblocked compound of formula I.

Modifications to the above processes may be necessary to accommodate the reactive functionalities of particular substituents. Such modifications would either be apparent or already known to one of ordinary skill in the art.

The following compounds are contemplated within the scope of the present invention:

(a) β-1-(2-Oxo-4-hydroxylamino-1,2-dihydropyrimidin-1-yl)-2-deoxy-2,2-difluororibose;

(b) β-(2-deoxy-2,2-difluoro-β-D-ribofuranosyl)-1,2,3,4-tetrazolo[1,5-c]pyrimidine-5(6H) -one;

(c) β-(2-deoxy-2,2-difluoro-β-D-ribofuranosyl)-1,2,4-triazolo[4,3-c]pyrimidine-3,5(2H, 6H)-dione;

(d) β-1-(2-Oxo-4-hydrazino-1,2-dihydropyrimidin-1-yl)-2-deoxy-2,2-difluororibose;

(e) β-1-(2-Oxo-4-aminocarboethoxy-1,2-dihydropyrimidin-1-yl)-2-deoxy-2,2-difluororibose;

(f) β-1-(2-Oxo-4-hydroxymethylamino-1,2-dihydropyrimidin-1-yl)-2-deoxy-2,2-difluororibose;

(g) β-1-(2-Oxo-4-N-glycinyl-1,2-dihydropyrimidin-1-yl)-2-deoxy-2,2-difluororibose;

(h) β-1-[2-Oxo-4-(2-methylhydrazino)-1,2-dihydropyrimidin-1-yl]-2-deoxy-2,2-difluororibose;

(i) β-1-(2-Oxo-4-N-glycine ethyl ester-1,2-dihydropyrimidin-1-yl)-2-deoxy-2,2-difluororibose;

(j) β-1-(2-Oxo-4-N-alanine ethyl ester-1,2-dihydropyrimidin-1-yl)-2-deoxy-2,2-difluororibose;

(k) β-1-(2-Oxo-4-methylamino-1,2-dihydropyrimidin-1-yl)-2-deoxy-2,2-difluororibose;

(l) β-1-(2-Oxo-4-ethylhydrazinocarboxylate-1,2-dihydropyrimidin-1-yl)-2-deoxy-2,2-difluororibose;

(m) β-(2-deoxy-2,2-difluoro-β-D-ribcfuranosyl)-1,2,3,4-tetrazolo[1,5-c]-8-methylpyrimidine-5(6H)-one;

(n) β-1-(2-Oxo-4-sulfhydryl-1,2-dihydropyrimidin-1-yl)-2-deoxy-2,2-difluororibose; and pharmaceutically acceptable salts thereof. The preferred compounds of formula I are compounds (a) thru (j) and pharmaceutically acceptable salts thereof.

Although generally neutral, particular compounds of formula I can possess sufficiently acidic or basic functional groups to react with any of a number of inorganic bases and inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid, sodium, potassium, lithium or ammonium acid addition salts and the like, organic acids such as p-toluene-sulfonic, methanesulfonic acid, oxalic acid, p-bromo-phenyl-sulfonic acid, carbonic acid, succinic acid, citric acid, benzoic acid, acetic acid, and the like. Examples of such pharmaceutically acceptable salts are sulfate, pyrosulfate, bisulfate, sulfite, bisulfite, phosphate, monohydrogenphosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, g-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It is recognized that various anomeric forms of the compound of formulas I and II may exist. This invention is not limited to any particular anomer but rather includes all possible individual anomers and mixtures thereof; preferred are the beta-anomers.

The compound of formula I and the pharmaceutically acceptable salts thereof can also exist as various solyates, such as with water, methanol, ethanol, dimethylformamide, and the like. Mixtures of such solyates can also be prepared. The source of such solrate can be from the solvent of crystallization, inherent in the solvent of preparation or crystallization, or adventitious to such solvent. These solyates are also within the scope of the present invention.

The pharmaceutically acceptable salts embraced by formula I of the present invention are prepared by reacting an equimolar or excess amount of an acid or base with a compound of formula I in a suitable mutual inert or substantially inert solvent or a mixture of solvents. The particular choice of solvent will depend on the relative solubility of the starting materials and resultant salts, and slurries rather than solutions of certain reagents may be used to obtain the salts. The salt forming reaction is carried out at about $-10°$ C. to about $100°$ C., preferably about room temperature and the solvent is removed by conventional means.

The following examples illustrate specific aspects of the present invention and are not intended to limit the scope thereof in any respect and should not be so construed.

EXAMPLE 1

β-1-(2-Oxo-4-hydroxyamino-1,2-dihydropyrimidin-1-yl)-2-deoxy-2,2-difluororibose

Triethylamine (0.093 g, 0.92 mmol) was added to a solution of β-1-(2-Oxo-4-(1,2,4-Triazol-1-yl) -1,2-dihydropyrimidin-1-yl)-3,5-bis-O -(t-butyldimethylsilyl)-2-deoxy-2,2-difluororibose (0.1 g, 0.18 mmol) and hydroxyamine hydrochloride (0.064 g, 0.92 mmol) in pdioxane (2.7 ml). The solution was stirred for 2 days at room temperature. The solvent was removed in vacuo and the residue was dissolved in ethyl acetate (10 ml) and washed twice with water (5 ml). The organic layer was dried over sodium sulfate and concentrated in vacuo to form an β-1-(2-Oxo-4-hydroxyamino-1,2-dihydropyrimidin -1-yl)-3,5-bis-O-(t-butyldimethylsilyl)-2-deoxy-2,2-difluororibose intermediate. The intermediate was deblocked by deblocking procedure (A) which gave 0.08 g of the titled product. (CD$_3$OD, 300 MHz ) δ3.7–4.0 (series of m, 3H); 4.27 (m, 1H); 5.99 (d, J=8Hz, 1H, H-5); 6.14 (dd, 1H, H-1'); 8.04 (d, J=8Hz, 1H, H-6); mass spectroscopy m/e=279=parent.

EXAMPLE 2

6-(2-deoxy-2,2-difluoro-β-D-ribofuranosyl)-1,2,3,4-tetrazolo[1,5-c]pyrimidine-5(6H) -one Chlorophenyl dichlorophosphate (0.16 g, 0.65 mmol) was added to a solution of β-1- (2,4-dioxo-1,2,3,4-tetrahydropyrimidin-1-yl)-3,5-di-O-acetyl-2 -deoxy-2,2-difluororibose (0.15 g, 0.43 mmol) in pyridine (4.0 ml). The solution was stirred overnight at room temperature. Lithium azide (0.032 g, 0.66 mmol) was added and the reaction mixture was again stirred overnight. The solvent was removed in vacuo and the residue was evaporated two times with toluene (5 ml). The residue was dissolved in ethyl acetate and washed with water, 1N hydrochloric acid, saturated sodium bicarbonate and twice with water. The organic layer was dried over sodium sulfate and the solvent removed in vacuo to form an 6-(2-deoxy-2,2-difluoro-3,5-di-O-acetyl-β-D-ribofuranosyl)-1,2,3,4-tetrazolo[1,5-c]pyrimidine-5(6H)-one intermediate. The intermediate was deblocked by deblocking procedure (C). The solvent was removed in vacuo and the residue purified on a reversed phase C18 chromatography column with water as eluent and evaporated in vacuo to give 0.016 g of the titled product. (CD$_3$OD, 300 MHz) δ3.57–4.05 (series of m, 3H); 4.38 (m, 1H); 6.38 (m, 1H, H-1'); 7.02 (d, J=8Hz, 1H, H-5); 8.18(d, J=8Hz, 1H, H-6); mass spectroscopy m/e=289=parent.

The compounds of Examples 3 thru 12 were prepared by substantially following the procedure in Example 1 and deblocking the resulting intermediate compound by the appropriate deblocking procedure.

EXAMPLE 3

β-1-(2-Oxo-4-ethylhydrazinocarboxylate-1,2-dihydropyrimidin-1-yl)-2-deoxy-2,2-difluororibose The β-1-(2-Oxo-4-ethylhydrazinocarboxylate-1,2-dihydropyrimidin-1-yl)-3,5-bis-O-(t -butyldimethylsilyl)-2-deoxy-2,2-difluororibose intermediate was deblocked by deblocking procedure (B). (Neat, 300 MHz) δ 1.25 (m, 3-H, —CH$_3$); 3.7–4.32 (series of m, 6H); 5.72 (d, J=8Hz, 1H, H-5); 6.19 (m, 1H, H-1') 7.3 (d, J=8Hz, 1H, H-6); mass spectroscopy m/e=350 =parent.

EXAMPLE 5

β-1-(2-Oxo-4-hydrazino-1,2-dihydropyrimidin-1-yl)-2-deoxy-2,2-difluororibose

The β-1-(2-Oxo-4-hydrazino-1,2-dihydropyrimidin-1-yl)-3,5-bis-O-(t-butyldimethylsilyl)-2-deoxy -2,2difluororibose intermediate was deblocked by deblocking procedure (A). (CD$_3$OD, 300 MHz) δ3.67–4.0 (two m, 3H); 4.28 (m, 1H); 5.97–6.23 (two m, 2H, H-5, H-1'); 8.13 (d, J=8Hz, 1H, H-6 ); mass spectroscopy m/e=279=parent.

EXAMPLE 6

β-1-(2-Oxo-4-aminocarboethoxy-1,2-dihydropyrimidin-1-yl)-2-deoxy-2,2-difluororibose The β-1-(2-Oxo-4-aminocarboethoxy-1,2-dihydropyrimidin-1-yl)-3,5-bis-O-(t-butyldimethYlsilyl) -2-deoxy-2,2-difluororibose intermediate was deblocked by deblocking procedure (A). (CD$_3$OD, 300 MHz) Δ1.28 (m, 3-H, —CH$_3$); 3.7–4.0 (two m, 3H); 4.2 (m, 3H) 6.22 (dd, 1H, H-1'); 7.3 (t, J=8Hz, 1H, H-5); 8.27 (d, J=8Hz, 1H, H-6); mass spectroscopy m/e=336 M+.

EXAMPLE 7

β-1-(2-Oxo-4-hydroxymethylamino-1,2-dihydropyrimidin-1-yl)-2-deoxy-2,2-difluororibose The β-1-(2-Oxo-4-hydroxymethylamino-1,2-dihydropyrimidin-1-yl)-3,5-bis-O-(t-butyldimethylsilyl) -2-deoxy-2,2-difluororibose intermediate was deblocked by deblocking procedure (A). (CD$_3$OD 300 MHz) δ3.6 (s, 3H, —CH$_3$) 3.73–4.0 (two m, 3H); 4.28 (m, 1H) 6.13 (dd, 1H, H-1'); 6.36 (d J=8Hz, 1H, H-5); 8.24 (d, J=8Hz, 1H, H-6); mass spectroscopy m/e=294=parent.

EXAMPLE 8

β-1- (2-Oxo-4-N-glycine ethyl ester-1,2-dihydropyrimidin-1-yl)-2-deoxy-2,2-difluororibose The β-1-(2-Oxo-4-N-glycine ethyl ester-1,2-dihydropyrimidin-1-yl)-3,5-bis-O-(t-butyldimethylsilyl) -2-deoxy-2,2-difluororibose intermediate was deblocked by deblocking procedure (A). (CD$_3$OD, 300 MHz) δ1.28 (t, 3H, —CH$_3$); 3.7–4.38 (series of m, 8-H); 6.18 (m, 1H, H-1'); 6.27 (d, J=8Hz, 1H, H-5); 8.27 (d, J=8Hz, 1H, H-6); mass spectroscopy m/e=350=parent.

EXAMPLE 9

β-1-(2-Oxo-4-N-glycinyl-1,2-dihydropyrimidin-1yl)-2-deoxy-2,2-difluororibose

The β-1-(2-Oxo-4-N-glycinyl-1,2-dihydropyrimidin-1-yl)-3,5-bis-O-(t-butyldimethylsilyl) -2- deoxy-2,2-difluororibose intermediate was deblocked by deblocking procedure (A). (CD$_3$OD, 300 MHz) δ3.78 (m, 1H) 3.94 (m, 2H); 4.2–4.4 (m, 3H); 6.15 (m, 1H, H-1'); 6.3 (d, J=8Hz, 1H, H-5); 8.24 (d, J=8Hz, 1H, H-6); mass spectroscopy m/e=321=parent

EXAMPLE 10

β-1-[2-Oxo-4-(2-methylhydrazino)-1,2-dihydropyrimidin-1-yl]-2-deoxy-2,2-difluororibose The β-1-(2-Oxo-4-(2-methylhydrazino)-1,2-dihydropyrimidin-1-yl)-3,5-bis-O-(t -butyldimethylsilyl)-2-deoxy-2,2-difluororibose intermediate was deblocked by deblocking procedure (B). (CD$_3$ OD, 300 MHz) δ3.33 (s, 3H, —CH$_3$); 3.7–4.0 (m, 3H); 4.21 (m, 1H); 6.2 (t, 1H, H-1'); 6.73 (d, J=8Hz, 1H, H-5 ); 7.78 (d, J=8Hz, 1H, H-6 ); mass spectroscopy m/e=292=parent.

EXAMPLE 11

β-1-(2-oxo-4-N-alanine ethyl ester-1,2-dihydropyrimidin-1-yl)-2-deoxy-2,2-difluororibose The β-1-(2-Oxo-4-N-alanine ethyl ester-1,2-dihydropyrimidin-1-yl)-3,5-bis-O-(t-butyldimethylsilyl) -2-deoxy-2,2-difluororibose intermediate was deblocked by deblocking procedure (A). (CD$_3$OD, 300 MHz) δ1.2.1 (t, 3H, —CH$_3$). 2.6 (t, 2H, —CH$_2$) (3.6–4.3 (series of m, 8H); 5.84 d, J=8Hz, 1H, H-5); 6.19 (m, 1H, H-1'); 7.74 (d, J=8Hz, 1H, H-6); mass spectroscopy m/e=363=parent.

EAMPLE 12

β-1-(2-Oxo-4-methylamino-1,2-dihydropyrimidin-1-yl)-2-deoxy-2,2-difluororibose

The β-1-(2-Oxo-4-methylamino-1,2-dihydropyrimidin-1-yl)-3,5-bis-O-(t-butyldimethylsilyl) -2-deoxy-2,2-difluororibose intermediate was deblocked by deblocking procedure (B). (CD$_3$OD, 300 MHz) δ2.86 (s, 3H, —CH$_3$) 3.7–3.95 (series of m, 3H); 4.22 (m, 1H, H-3'); 5.83 (d, J=8Hz, 1H, H-5); 6.19 (m, 1H, H-1'); 7.72 (d, J=8Hz, 1H, H-6); mass spectroscopy m/e=277=parent.

The compound of Example 13 was prepared by the procedure described in Example 2.

EXAMPLE 13

6-(2-deoxy-2,2-difluoro-β-D-ribofuranosyl)-1,2,3,4-tetrazolo[1,5-c]-8-methylpyrimidine-5(6H)-one The 6-(2-deoxy-2,2-difluoro-3,5-di-O-acetyl-β-D-ribofuranosyl)-1,2,3,4-tetrazolo[1,5-c]-8-methylpyrimidine-5(6H)-one intermediate was deblocked by deblocking procedure (C). (CD$_3$OD, 300 MHz) δ2.37 (s, 3-H, —CH$_3$); 3.78–4.2 (series of m, 3H); 4.4 (m, 1H, H-3'); 6.37 (m, 1H, H-1'); 7.98 (s, 1H, H-6); mass spectroscopy m/e=303=parent.

EXAMPLE 14

β-1-(2-Oxo-4-sulfhydryl-1,2-dihydropyrimidin-1-yl)-2-deoxy-2,2-difluororibose

Phosphorus pentasulfide (0.24 g, 0.53 mmol) was added to a solution of β-1-(2,4-dioxo-1,2,3,4-tetrahydropyrimidin-1-yl)-3,5-di-O-acetyl-2-deoxy -2,2-difluororibose (0.174 g, 0.5 mmol) in dioxane (7.0 ml) and the suspension was refluxed for 5 hours. The reaction mixture was cooled to ambient temperature, the insolubles filtered and discarded and the filmrate was concentrated in vacuo to a residue which was purified by column chromatography on silica gel using hexane/ethyl acetate 3:2. The resulting β-1-(2-Oxo-4-sulfhydryl-1,2-dihydropyrimidin-1-yl) -3,5-di-O-acetyl-2- deoxy-2,2-difluororibose intermediate was deblocked with sodium hydroxide (2 N, 5.0 mol equiv.) in ethanol at ambient temperature and purified by normal phase column chromatography using ethyl acetate to give 0.14 g of the titled product. (CD$_3$OD, 300 MHz) δ3.67–3.96 (series of m, 3H); 4.18–4.34 (m, 1H, H-3'); 6.08 (m, 1H, H-1'); 6.15 (d, J=8Hz, 1H, H-5); 7.64 (d, J=8Hz, 1H, H-6) mass spectroscopy m/e=280=parent.

As noted above, the compounds of formula I are useful for treating mammals suffering from disease states stemming from tumors and viral infections. Therefore, another embodiment of the present invention is a method for treating mammals suffering from disease states stemming from tumors and viral infections and comprises administering to said mammal an effective amount of a compound of formula I or pharmaceutically acceptable salt thereof.

The treatment contemplated by the present method includes both medical therapeutic and/or prophylactic treatment, as appropriate. The specific dosage level of the compound administered according to this invention will, of course, be determined by the circumstances surrounding the case, including, for example, the particular compound administered, the route of administration, and the condition being treated. A typical daily dosage contains from about 1 mg/M$^2$ to about 1,000 mg/M$^2$ of the compound of formula I.

The compounds of formula I can be administered by a variety of routes including oral, rectal, transdermal, subcutaneous, intravenous, intramusclar, and intranasal.

The compounds of formula I are preferably formulated prior to administration. Therefore, another embodiment of the present invention is a pharmaceutical formulation or composition comprising an effective amount of a compound of formula I or a pharmaceutically acceptable salt thereof and a pharmaceutically acceptable carrier, diluent or excipient therefore.

The active ingredient in such formulations comprises from 0.1 percent to 99.9 percent by weight of the formulation.

The present pharmaceutical formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10 percent by weight of the active compound, soft and hard gelatin capsules, suppositories, sterile injectable solutions, sterile packaged powders, and the like.

Examples of suitable carriers, excipients, and diluents are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methylhydroxybenzoates, propylhydroxybenzoates, talc, magnesium stearate and mineral oil. The formulations may additionally include lubricating agents, wetting agents, sweetening agents, flavoring agents, emulsifying and suspending agents, preserving agents, and the like. The compositions of the invention may be formulated so as to provide quick, sustained or delayed release of the active ingredient after administration to the patient by employing procedures well known in the art.

The compositions are preferably formulated in a unit dosage or, each dosage generally containing form about 0.1 mg to about 3,000 mg, and preferably from about 1 mg to about 500 mg, of the active ingredient. However, it will be understood that the amount of compound actually administered will be determined by a physician, in the light of the relevant circumstances including the condition to be treated, the particular compound to be administered, the chosen route of administration, the age, weight, and response of the individual patient, and the severity of the patient's symptoms, and therefore the above dosage ranges are not intended to limit the scope of the invention in any way.

The following formulation examples are illustrative of specific pharmaceutical formulations employing compounds comprehended by the present method and are not intended to limit the scope of the invention in any way.

FORMULATION 1

Hard gelatin capsules are prepared using the following ingredients:

|  | Quantity (mg/capsule) |
| --- | --- |
| Active ingredient | 250 |
| Starch, dried | 200 |
| Magnesium | 10 |
| Total | 460 mg |

The above ingredients are mixed and filled into hard gelatin capsules in 460 mg quantities.

FORMULATION 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearate acid | 5 |
| Total | 665 mg |

The components are blended and compressed to form tablets each weighing 665 mg.

FORMULATION 3

An aerosol solution is prepared containing the following components:

|  | Weight Percent |
| --- | --- |
| Active ingredient | 0.25 |
| Ethanol | 29.75 |
| Propellant 22 (Chlorodifluoromethane) | 70.00 |

The active compound is mixed with ethanol and the mixture added to a portion of the propellant 22, collected to −30° C. and transferred to a filling device. The required amount is then placed in a stainless steel container and diluted with the remainder of the propellanE. The valve units are then fitted to the container.

FORMULATION 4

Tablets, each containing 60 mg of active ingredient, are made as follows:

| Active ingredient | 60 mg |
|---|---|
| Starch | 45 mg |
| Microcrystalline cellulose | 35 mg |
| Polyvinylpyrrolidonne (10% solution water) | 4 mg |
| Sodium carboxymethyl starch | 4.5 mg |
| Magnesium stearate starch | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

FORMULATION 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, such containing 50 mg of active ingredient per 5 ml dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| Active ingredient | 100 mg |
|---|---|
| Sodium alginate | 500 mg |
| Isotonic saline | 1,000 ml |

The solution of the above ingredients generally is administered intravenously to a subject at a rate of 1 ml per minute.

Anti-Cancer Test Data

The compounds of formula I and their pharmaceutically acceptable salts are surprisingly advantageous for treating mammals suffering from disease states stemming from tumors. The activity of representative compounds employed in the present invention has been demonstrated in standard screens commonly used by those in the art to test compounds for potential use as solid and nonsolid anti-tumor drugs. For example, these screens have been used to demonstrate the anti-tumor activity of commercially available cancer drugs such as the vinca alkaloids; see Miller, et al., *J. Med. Chem.*, Vol. 20, No. 3, 409 (1977) and Sweeney, et al., *Cancer Research*, vol. 38, 2886 (1978). The representative compounds of formula I employed in the present invention are cytotoxic as They inhibit the growth of rapidly dividing human leukemia cells (CCRF-CEM cell line). Table 1 below gives the results of testing several compounds representative of formula I. In Table 1, Column 1 gives the representative compound and Column 2 gives the $IC_{50}$ (concentration giving 50 percent growth inhibition) in μg/ml. A compound having an $IC_{50}$ less than 20 μg/ml is considered to be active.

TABLE 1

| Compound | $IC_{50}$ (μg/ml) |
|---|---|
| β-1-(2-Oxo-4-hydrazion-1,2-dihydropyrimidin-1-yl)-2-deoxy-2,2-difluororibose (Example 5) | 0.077 |
| β-1-[2-Oxo-4-(2-methylhydrazino)-1,2-dihydropyrimidin-1-yl]-2-deoxy-2,2-difluororibose (Example 10) | 4.1 |
| β-1-(2-Oxo-4-hydroxylamino-1,2-dihydropyrimidin-1-yl)-2-deoxy-2,2-difluororibose (Example 1) | 0.086 |
| β-1-(2-Oxo-4-hydroxymethylamino-1,2-dihydropyrimidin-1-yl)-2-deoxy-2,2-difluororibose (Example 7) | 0.3 |
| β-1-(2-Oxo-4-aminocarboethoxy-1,2-dihydropyrimidin-1-yl)-2-deoxy-2,2-difluororibose (Example 6) | 0.051 |
| β-1-(2-Oxo-4-N-glycine ethyl ester-1,2-dihydropyrimidin-1-yl)-2-deoxy-2,2-difluororibose (Example 8) | 18.4 |
| β-1-(2-Oxo-4-N-alanine ethyl ester-1,2-dihydropyrimidin-1-yl)-2-deoxy-2,2-difluororibose | 6.3 |

TABLE 1-continued

| Compound | IC₅₀ (μg/ml) |
|---|---|
| (Example 11) | |
| β-1-(2-Oxo-4-N-glycinyl-1,2-dihydropyrimidin-1-yl)-2-deoxy-2,2-difluororibose (Example 9) | 0.4 |
| 6-(2-deoxy-2,2-difluoro-β-D-ribofuranosyl)-1,2,4-triazolo[4,3c]pyrimidine-3,5(2H,6H-dione (Example 4) | 0.2 |
| 6-(2-deoxy-2,2-difluoro-β-D-ribofuranosyl)-1,2,3,4-tetrazolo[1,5-c]pyrimidine-5(6H)-one (Example 2) | 0.5 |

Anti-Viral Test Data

The compounds of formula I are also effective for the treatment of vital infections and can be used to treat or prevent infections and caused by a wide range of viruses; and more particularly, infections caused by viruses of the Herpes genus. Typical viruses against which the compounds of formula I can be used include all A and B strains of influenza, para-influenza, respiratory syncytial viruses, various Herpes I and Herpes II strains, Echo and vaccinia viruses, measles, Semkki Forest and retroviruses such as Friends Leukemia Virus. The compounds of formula I are used for treating vital infections in the manner usual in the treatment of such pathologies. The anti-viral effect of the compounds of formula I has been shown by proven in vitro test described below carried out for representative compounds.

African green monkey kidney cells (BSC-1) were grown in 25 cm² Falcon flasks at 37° C. in medium 199 with 5% inactivated fetal bovine serum (FBS), penicillin (150 units/ml) and streptomycin (150 μg/ml). When confluent monolayers were formed, the supernatant growth medium was removed and 0.3 ml of an appropriate dilution of pseudorabies virus or Herpes simplex virus, types I and II (HSV-1 and HSV-2), was added to each flask. After adsorption for one hour at room temperature, the virus infected cell sheet was overlaid with a medium comprising one part 1 percent Ionagar No. 2 and one part double strength medium 199 with FCS (fetal calf serum), penicillin, and streptomycin and also containing a representative compound am concentrations ranging from 100 μg/ml to 0.39 μg/ml. A flask containing no representative compound served as a control. The stock solution of representative compound was made up in dimethylsulfoxide at a concentration of 104 μg/ml. The flasks were incubated for 72 hours at 37° C. Plaques were seen in those areas where the virus infected and reproduced in the cells. A solution of 10 percent formalin and 2 percent sodium acetate was added to each flask to inactivate the virus and fix the cell sheet to the surface of the flask. The virus plaques, irrespective of size, were counted after staining the surrounding cell areas with crystal violet. The plaque count was compared to the control count at each drug concentration. The activity of the compound was expressed as percentage plaque inhibition. Table 2 below gives the results of testing several representative compounds of formula I. In Table 2, Column 1 gives the representative compound and Column 2 gives the IC₅₀ (concentration giving 50 percent growth inhibition) in μg/ml. A compound having an IC₅₀ less than 20 μg/ml is considered to be active.

TABLE 2

| Compound | HSV-1 (μg/ml) | HSV-2 (μg/ml) |
|---|---|---|
| β-1-(2-Oxo-4-hydrazino-1,2-dihydropyrimidin-1-yl)-2-deoxy-2,2-difluororibose (Example 5) | 3.12 | 4.35 |
| β-1-(2-Oxo-4-hydroxylamino-1,2-dihydropyrimidin-1-yl)-2-deoxy-2,2-difluororibose (Example 1) | 0.7 | 1.07 |
| β-1-(2-Oxo-4-hydroxymethylamino-1,2-dihydropyrimidin-1-yl)-2-deoxy-2,2-difluororibose (Example 7) | 18.0 | 11.1 |
| β-1-(2-Oxo-4-aminocarboethoxy-1,2-dihydropyrimidin-1-yl)-2-deoxy-2,2-difluororibose (Example 6) | 0.53 | 0.58 |
| 6-(2-deoxy-2,2-difluoro-β-D-ribofuranosyl)-1,2,4-triazolo[4,3c]pyrimidine-3,5(2H,6H)-dione (Example 4) | 6.0 | 4.9 |
| 6-(2-deoxy-2,2-difluoro-β-D-ribofuranosyl)-1,2,3,4-tetrazolo[1,5-c]pyrimidine-5(6H)-one (Example 2) | 8.0 | 9.25 |

The present invention has been described in detail, including the preferred embodiments thereof. However, it will be appreciated that those skilled in the art, upon consideration of the present disclosure, may make modifications and/or improvements on this invention that fall within the scope and spirit of the invention as set forth in the following claims.

What is claimed is:

1. A compound of the formula

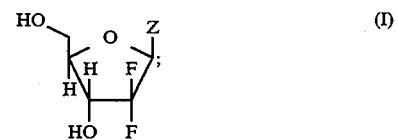

wherein Z is a nucleobase selected from the group consisting of:

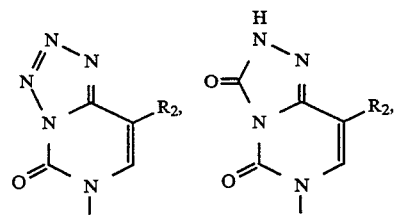

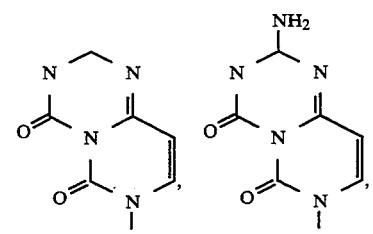

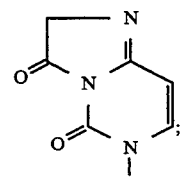

wherein R₁ is selected from the group consisting of glycine, thio, hydrogen, hydrazine, 2-methylhydrazino, ethylhydrazino carboxylate, hydroxyamino, hydroxymethylamino, carboxylic acid, carboxaldehyde, isocyano, cyanate, carboethoxyamino, aminosulfonyl, glycine ethyl ester, alanine ethyl ester, carbonitrile, aminothio, aminomethyl, and sulfonylamino; and R₂ is selected from the group consisting of hydrogen, methyl, bromo, fluoro, chloro, iodo, bromovinyl, amino and pharmaceutically acceptable salts thereof.

2. A compound according to claim 1 wherein R₁ is selected from the group consisting of hydrazine, hydroxyamino, carboethoxyamino, hydroxymethylamino, glycine, 2-methylhydrazino, alanine ethyl ester, and glycine ethyl ester.

3. A compound according to claim 1 wherein Z is selected from 1,2,3,4 -tetrazolo [1,5-c]pyrimidine-5(6H)-one and 1,2,3,4-tetrazolo[1,5-c]-8-methylpyrimidine-5(6H)-one.

4. A compound according to claim 1 selected from the group consisting of:
 (a) 1-(2-Oxo-4-hydroxylamino-1,2-dihydropyrimidin-1-yl)-2-deoxy-2,2-difluororibose;
 (b) 6-(2-deoxy-2,2-difluoro-β-D-ribofuranosyl)-1,2,3,4-tetrazolo[1,5-c]pyrimidine-5(6H) -one;
 (c) 6-(2-deoxy-2,2-difluoro-β-D-ribofuranosyl)-1,2,4-triazolo[4,3-c]pyrimidine-3,5(2H,6H)dione;
 (d) β-1-(2-Oxo-4-hydrazino-1,2-dihydropyrimidin-1-yl)-2-deoxy-2,2-difluororibose;
 (e) β-1-(2-Oxo-4-aminocarboethoxy-1,2-dihydropyrimidin-1-yl)-2-deoxy-2,2-difluororibose;
 (f) β-1-(2-Oxo-4-hydroxymethylamino-1,2-dihydropyrimidin-1-yl)-2-deoxy-2,2-difluororibose;
 (g) β-1-(2-Oxo-4-N-glycinyl-1,2-dihydropyrimidin-1-yl)-2-deoxy-2,2-difluororibose;
 (h) β-1-[2-Oxo-4-(2-methylhydrazino)-1,2-dihydropyrimidin-1-yl]-2-deoxy -2,2-difluororibose;
 (i) β-1-(2-Oxo-4-N-glycine ethyl ester-1,2-dihydropyrimidin-1-yl)-2-deoxy-2,2-difluororibose;
 (j) β-1-(2-Oxo-4-N-alanine ethyl ester-1,2-dihydropyrimidin-1-yl)-2-deoxy-2,2-difluororibose;
 (k) β-1-(2-Oxo-4-ethylhydrazinocarboxylate-1,2-dihydropyrimidin-1-yl)-2-deoxy-2,2-difluororibose;
 (l) 6-(2-deoxy-2,2-difluoro-β-D-ribofuranosyl)-1,2,3,4-tetrazolo[1,5-c]-8-methylpyrimidine -5(6H) -one; and
 (m) β-1-(2-Oxo-4-sulfhydryl-1,2-dihydropyrimidin-1-yl)-2-deoxy-2,2-difluororibose; and pharmaceutically acceptable salts thereof.

5. A pharmaceutical composition useful for treating susceptible leukemias and viral infections in mammals comprising a suitable pharmaceutically acceptable carrier, diluent or excipient and a compound of claim 1.

6. A pharmaceutical composition according to claim 5 wherein R₁ is selected from the group consisting of hydrazine, hydroxyamino, cavboethoxyamino, hydroxymethylamino, glycine, 2-methylhydrazino, alanine ethyl ester, and glycine ethyl ester.

7. A pharmaceutical composition according to claim 5 wherein Z is selected from 1,2,3,4-tetrazolo[1,5c-]pyrimidine-5(6H)-one and 1,2,3,4-tetrazolo[1,5-c]-8-methylpyrimidine -5(6H)-one.

8. A pharmaceutical composition according to claim 5 wherein the compound is selected from the group consisting of:
 (a) β-1-(2-Oxo-4-hydroxylamino-1,2-dihydropyrimidin-1-yl)-2-deoxy-2,2-difluororibose;
 (b) 6-(2-deoxy-2,2-difluoro-β-D-ribofuranosyl)-1,2,3,4-tetrazolo[1,5-c]pyrimidine-5(6H) -one;
 (c) 6-(2-deoxy-2,2-difluoro-β-D-ribofuranosyl)-1,2,4-triazolo[4,3-c]pyrimidine-3,5(2H, 6H)-dione;
 (d) β-1-(2-Oxo-4-hydrazino-1,2-dihydropyrimidin-1-yl)-2-deoxy-2,2-difluororibose;
 (e) β-1-(2-Oxo-4-aminocarboethoxy-1,2-dihydropyrimidin-1-yl)-2-deoxy-2,2-difluororibose;
 (f) β-1-(2-Oxo-4-hydroxymethylamino-1,2-dihydropyrimidin-1-yl)-2-deoxy-2,2-difluororibose;
 (g) β-1-(2-Oxo-4-N-glycinyl-1,2-dihydropyrimidin-1-yl)-2-deoxy-2,2-difluororibose;
 (h) β-1-(2-Oxo-4-(2-methylhydrazino)-1,2-dihydropyrimidin-1-yl]-2-deoxy-2,2-difluororibose;
 (i) β-1-(2-Oxo-4-N-glycine ethyl ester-1,2-dihydropyrimidin-1-yl)-2-deoxy-2,2-difluororibose;
 (j) β-1-(2-Oxo-4-N-alanine ethyl ester-1,2-dihydropyrimidin-1-yl)-2-deoxy-2,2-difluororibose;
 (k) β-1-(2-Oxo-4-ethylhydrazinocarboxylate-1,2-dihydropyrimidin-1-yl)-2-deoxy-2,2-difluororibose;
 (l) 6-(2-deoxy-2,2-difluoro-β-D-ribofuranosyl)-1,2,3,4-tetrazolo[1,5-c]-8-methylpyrimidine -5(6H)-one;
 (m) β-1-(2-Oxo-4-sulfhydryl-1,2-dihydropyrimidin-1-yl)-2-deoxy-2,2-difluororibose.

9. An intermediate of the formula

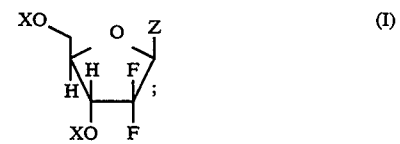

wherein Z is a nucleobase selected from the group consisting of:

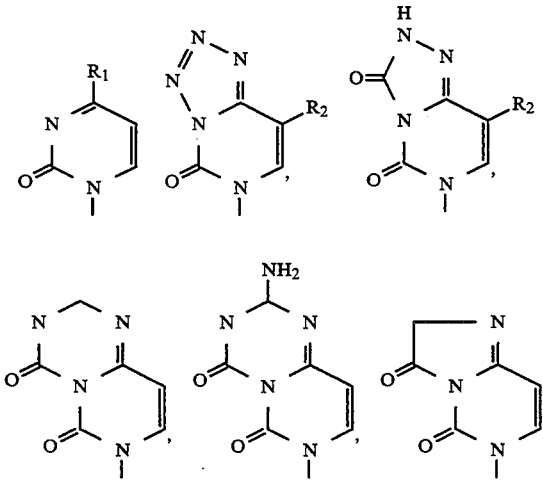

wherein R₁ is selected from the group consisting of glycine, thio, hydrogen, hydrazine, methylamino, 2-methylhydrazino, ethylhydrazino carboxylate, hydroxyamino, hydroxymethylamino, carboxylic acid, carboxaldehyde, isocyano, cyanate, carboethoxyamino, aminosulfonyl, glycine ethyl ester, alanine ethyl ester, carbonitrile, aminothio, aminomethyl, and sulfonylamino; and R₂ is selected from the group consisting of hydrogen, methyl, bromo, fluoro, chloro, iodo, bromovinyl and, amino and X is a hydroxy protecting group.

10. An intermediate according to claim 9 wherein $R_1$ is selected from the group consisting of hydrazine, hydroxyamino, carboethoxyamino, hydroxymethylamino, glycine, 2-methylhydrazino, alanine ethyl ester, and glycine ethyl ester.

11. An intermediate according to claim 9 wherein Z is selected from 1,2,3,4-tetrazolo[1,5-c]pyrimidine-5(6H)-one and 1,2,3,4-tetrazolo[1,5-c]-8-methylpyrimidine-5(6H)-one.

12. An intermediate according to claim 9 wherein the hydroxyprotecting group consisting of acetyl and t-butyldimethylsilyl.

13. The intermediate of claim 9 wherein the intermediate is selected from the group consisting of:
(a) β-1-(2-Oxo-4-hydroxylamino-1,2-dihydropyrimidin-1-yl)-3,5-bis-O-(t-butyldimethylsilyl)-2-deoxy-2,2-difluororibose;
(b) 6-(2-deoxy-2,2-difluoro-3,5-di-O-acetyl-β-D-ribofuranosyl)-1,2,3,4-tetrazolo[1,5-c]pyrimidine-5(6H)-one;
(c) 6-(2-deoxy-2,2-difluoro-5-D-ribofuranosyl)-1,2,4-triazolo[4,3-c]pyrimidine-3,5(2H,6H)-dione;
(d) β-1-(2-Oxo-4-hydrazino-1,2-dihydropyrimidin-1-yl)-3,5-bis-O-(t-butyldimethylsilyl)-2-deoxy-2,2-difluororibose;
(e) β-1-(2-Oxo-4-aminocarboethoxy-1,2-dihydropyrimidin-1-yl)-3,5-bis-O-(t-butyldimethylsilyl)-2-deoxy-2,2-difluororibose;
(f) β-1-(2-Oxo-4-hydroxymethylamino-1,2-dihydropyrimidin-1-yl)-3,5-bis-O-(t-butyldimethylsilyl)-2-deoxy-2,2-difluororibose;
(g) β-1-(2-Oxo-4-N-glycinyl-1,2-dihydropyrimidin-1-yl)-3,5-bis-O-(t-butyldimethylsilyl)-2-deoxy-2,2-difluororibose;
(h) β-1-(2-Oxo-4-(2-methylhydrazino)-1,2-dihydropyrimidin-1-yl]-3,5-bis-O-(t-butyldimethylsilyl)-2-deoxy-2,2-difluororibose;
(i) β-1-(2-Oxo-4-N-glycine ethyl ester-1,2-dihyclropyrimidin-1-yl)-3,5-bis-O-(t-butyldimethylsilyl)-2-deoxy-2,2-difluororibose;
(j) β-1-(2-Oxo-4-N-alanine ethyl ester-1,2-dihydropyrimidin-1-yl)-3,5-bis-O-(t-butyldimethylsilyl)-2-deoxy-2,2-difluororibose;
(k) β-1-(2-Oxo-4-methylamino-1,2-dihydropyrimidin-1-yl)-3,5-bis-O-(t-butyldimethylsilyl)-2-deoxy-2,2-difluororibose;
(l) β-1-(2-Oxo-4-ethylhydrazinocarboxylate-1,2-dihydropyrimidin-1-yl)-3,5-bis-O-(t-butyldimethylsilyl)-2-deoxy-2,2-difluororibose;
(m) 6-(2-deoxy-2,2-difluoro-3,5-di-O-acetyl-5-Dribofuranosyl)-1,2,3,4-tetrazolo[1,5-c]-8-methylpyrimidine-5(6H)-one;
(n) β1-(2-Oxo-4-sulfhydryl-1,2-dihydropyrirnidin-1-yl)-3,5-bis-O-(t-butyldimethylsilyl)-2-deoxy-2,2-difluororibose.

* * * * *

UNITED STATES PATENT AND TRADEMARK OFFICE
CERTIFICATE OF CORRECTION

PATENT NO. : 5,430,026

DATED : July 4, 1995

INVENTOR(S) : Larry Hertel; Julian S. Kroin

It is certified that error appears in the above-identified patent and that said Letters Patent is hereby corrected as shown below:

In the title, and on Column 1, lines 1-6, delete original title and insert in its place --2'-DEOXY-2',2'-DIFLUORO-4-(SUBSTITUTED)PYRIMIDINE NUCLEOSIDES, BICYCLIC DERIVATIVES, PHARMACEUTICAL COMPOSITIONS, AND SYNTHETIC PRECURSORS--.

Column 3, line 31, delete "Nucleosides, Org. them.," and insert in its place --Nucleosides, J. Org. Chem.,--.

Column 3, line 34, delete "(t-butYldimethylsilyl)" and insert in its place --(t-butyldimethylsilyl)--.

Column 4, line 9, delete "*ProteCtive*" and insert in its place --*Protective*--.

Column 5, line 66, delete "solrate" and insert in its place --solvate--.

Column 6, line 1, delete "solyates" and insert in its place --solvates--.

Column 6, line 27, delete "pdioxane" and insert in its place --p-dioxane--.

Column 7, line 13, delete "6 1.25" and insert in its place --$\delta$ 1.25--.

Column 7, line 21, delete "-2-deoxy    -2,2di" and insert in its place --2-deoxy-2,2-di--.

Column 7, line 32, delete "(t-butyldimethYlsilyl)" and insert in its place --(t-butyldimethylsilyl)--.

Column 7, line 35, delete "$\Delta$1.28" and insert in its place --$\delta$1.28--.

Column 7, line 64, delete "-1yl)" and insert in its place ---1-yl)--.

Column 8, line 25, delete "$\delta$1.2.1" and insert in its place --$\delta$1.21--.

Column 8, line 26, delete "5.84d," and insert in its place --5.84(d--.

Column 8, line 64, delete "filmrate" and insert in its place --filtrate--.

Column 10, line 7, delete "form" and insert in its place --from--.

Column 11, lines 1-2, delete "propellanE" and insert in its place --propellant--.

Column 11, line 64, delete "5 mi" and insert in its place --5 ml--.

Column 12, line 44, delete "They" and insert in its place --they--.

UNITED STATES PATENT AND TRADEMARK OFFICE
CERTIFICATE OF CORRECTION

PATENT NO. : 5,430,026

DATED : July 4, 1995

INVENTOR(S) : Larry Hertel; Julian S. Kroin

It is certified that error appears in the above-identified patent and that said Letters Patent is hereby corrected as shown below:

Column 12, line 56, delete "hydrazion" and insert in its place --hydrazino--.

Column 13, line 16, delete "vital" and insert in its place --viral--.

Column 13, line 46, delete "am" and insert in its place --at--.

Column 15, line 2, delete "hydrazinc, 2-methylhydrazlno" and insert in its place --hydrazine, 2-methylhydrazino--.

Column 15, line 7, delete "sulfonylamlno" and insert in its place --sulfonylamino--.

Column 15, line 12, delete "hydrazinc" and insert in its place --hydrazino--.

Column 15, line 14, delete "glycine" and insert in its place --glycinyl--.

Column 15, line 14, delete "alanlne" and insert in its place --alanine--.

Column 15, line 15, delete "glyclne" and insert in its place --glycine--.

Column 15, line 22, delete "(a) 1-(2-" and insert in its place --(a) $\beta$-1-(2---.

Column 15, line 27, delete "(2H,6H)dione" and insert in its place --(2H,6H)-dione--.

Column 15, line 57, delete "hydrazine" and insert in its place --hydrazino--.

Column 15, line 57, delete "cavboethoxyamino" and insert in its place --carboethoxyamino--.

Column 15, line 58, delete "glycine" and insert in its place --glycinyl--.

Column 16, line 13, delete "$\beta$-1-2-Oxo" and insert in its place --$\beta$-1-(2-Oxo--.

Column 16, line 25, after the word "one;" insert --and--.

Column 17, line 4, delete "hydrazine" and insert in its place --hydrazino--.

Column 17, line 7, delete "glycine" and insert in its place --glycinyl--.

Column 17, line 26, delete "difluoro-5-D" and insert in its place --difluoro-$\beta$-D--.

UNITED STATES PATENT AND TRADEMARK OFFICE
CERTIFICATE OF CORRECTION

PATENT NO. : 5,430,026

DATED : July 4, 1995

INVENTOR(S) : Larry Hertel; Julian S. Kroin

It is certified that error appears in the above-identified patent and that said Letters Patent is hereby corrected as shown below:

Column 18, line 13, delete "2-dihycl-" and insert in its place --2-dihyd---.

Column 18, line 25, delete "acetyl-5-" and insert in its place --acetyl-β---.

Column 18, line 26, delete "Dribofuranosyl" and insert in its place --D-ribofuranosyl--.

Column 18, line 27, delete "one;" and insert in its place --one; and--.

Column 18, line 28, delete "β1-(2" and insert in its place --β-1-(2--.

Column 18, line 28, delete "dihydropyriridin" and insert in its place --dihydropyrimidin--.

Signed and Sealed this

Sixth Day of January, 1998

Attest:

BRUCE LEHMAN

Attesting Officer

Commissioner of Patents and Trademarks